United States Patent [19]
Lampropoulos et al.

[11] Patent Number: 5,581,038
[45] Date of Patent: Dec. 3, 1996

[54] PRESSURE MEASUREMENT APPARATUS HAVING A REVERSE MOUNTED TRANSDUCER AND OVERPRESSURE GUARD

[75] Inventors: Fred P. Lampropoulos, Salt Lake City, Utah; Manuel G. Rossell, San Jose, Calif.

[73] Assignee: Sentir, Inc., Santa Clara, Calif.

[21] Appl. No.: 222,904

[22] Filed: Apr. 4, 1994

[51] Int. Cl.$^6$ .................... G01L 9/06; A61B 5/02
[52] U.S. Cl. .................... 73/727; 73/721; 73/756; 128/675
[58] Field of Search .................... 73/721, 727, 708, 73/715, 753, 756; 128/672, 675

[56] References Cited

U.S. PATENT DOCUMENTS

| | | | |
|---|---|---|---|
| 4,198,989 | 4/1980 | Hawke et al. | 128/675 |
| 4,320,664 | 3/1982 | Rehn et al. | 73/708 |
| 4,465,075 | 8/1984 | Swartz | 128/672 |
| 4,576,181 | 3/1986 | Wallace et al. | 128/675 |
| 4,586,382 | 5/1986 | Sinha | 73/703 |
| 4,658,651 | 4/1987 | Le | 73/708 |
| 4,691,575 | 9/1987 | Sonderegger et al. | 73/756 |
| 4,763,098 | 8/1988 | Glenn et al. | 338/4 |
| 4,823,605 | 4/1989 | Stein | 73/727 |
| 4,825,876 | 5/1989 | Beard | 128/675 |
| 5,074,947 | 12/1991 | Estes et al. | 156/307 |
| 5,086,777 | 2/1992 | Hishii | 128/675 |
| 5,105,820 | 4/1992 | Moriuchi et al. | 128/675 |
| 5,196,371 | 3/1993 | Kulesza et al. | 437/183 |
| 5,220,838 | 6/1993 | Fung et al. | 73/721 |
| 5,341,684 | 8/1994 | Adams et al. | 73/756 |

*Primary Examiner*—Richard Chilcot
*Assistant Examiner*—Paul D. Amrozowicz
*Attorney, Agent, or Firm*—Workman, Nydegger & Seeley

[57] ABSTRACT

A novel pressure measurement apparatus for measuring fluid pressures generated within a fluid passageway is disclosed. The apparatus includes a semiconductor pressure transducer which is mounted to a chip carrier comprised of a ceramic substrate layer. The semiconductor pressure transducer is reverse mounted to the substrate layer by way of a series of electrically conductive epoxy bond points. The semiconductor pressure transducer is enclosed within a gel cap containing an incompressible gel medium. Fluid pressures generated within the fluid passageway are communicated to the transducer via the gel medium.

15 Claims, 6 Drawing Sheets

PRESSURE MEASUREMENT APPARATUS HAVING A REVERSE MOUNTED TRANSDUCER AND OVERPRESSURE GUARD

BACKGROUND

1. Field of the Invention

The present invention relates to a pressure measurement apparatus for measuring a fluid pressure. More particularly, the present invention relates to a pressure measurement apparatus having a semiconductor pressure transducer that is reverse mounted to a carrier substrate.

2. Background Art

Medical applications, complex manufacturing processes, automotive operations and a myriad of related areas require various fluid pressures to be monitored in a manner that is reliable, accurate, low in cost and easy to implement. Typically, pressure transducers are utilized to provide this function. These transducers are devices that convert the physical variable—pressure—into a corresponding electrical signal.

A standard pressure transducer is usually comprised of a thin diaphragm which is capable of being deflected by an applied pressure, the magnitude of which is to be measured. A mechanism is then provided for measuring the amount of deflection of the diaphragm, the degree of deflection being representative of the magnitude of the applied pressure. This measuring mechanism is usually made up of suitable electronic circuitry which is configured so as to generate an electrical signal that is reflective of the pressure exerted on the diaphragm. The electrical signal is then supplied to a monitoring device, which then displays, or otherwise responds to, the applied pressure.

Typically, the electronic measuring mechanism used to measure the deflection of the diaphragm is comprised of a resistive strain gauge that is disposed on the diaphragm. The resistive strain gauge is made up of a combination of resistive wires that are usually arranged in a standard Wheatstone Bridge configuration. The wires are then stretched (or compressed, depending on how they are oriented on the diaphragm) when the diaphragm is deflected by the pressure force. In compliance with standard electrical principles, this tensile force causes the electrical resistance of the wires to change. Thus, by applying a constant voltage across the circuit, any change in the wires' resistance will result in a corresponding change in the electrical current through the wires in accordance with Ohm's law. This electrical current is representative of the amount by which the diaphragm has been deflected, and can be used to determine the magnitude of the applied pressure.

Increasingly, pressure transducers of this type have been constructed using standard semiconductor fabrication techniques. The goal has been to produce transducers that are reduced in size, that are more accurate and reliable and that are more easily manufactured in mass quantities, thereby reducing individual transducer costs. Transducers of this type have the required resistive elements formed on the surface of a single, bonded silicone chip, by using conventional ion implanting or diffusion techniques. A portion of the chip is then etched away by using chemicals or other standard etching methods, so as to form a thin diaphragm. When a pressure is applied to this diaphragm, the resistances of the diffused resistors vary by the piezoresistive effect in proportion to the applied pressure. Thus, a single silicon chip can be formed to comprise both the pressure diaphragm and the measuring circuitry of a pressure transducer.

This approach to constructing a pressure transducer from a semiconductor, although advantageous in many respects, also creates additional problems which must be addressed. For example, in such devices, the semiconductor transducer chip must be physically mounted on a chip carrier in a manner such that the diaphragm can be coupled to the fluid pressure that is to be measured. At the same time, the transducer chip must be electrically connected to the chip carrier in a manner such that the necessary voltage may be supplied to the resistive elements and in a manner such that the resultant pressure signal can be accessed by the monitoring equipment.

Also, the accuracy of a semiconductor transducer is temperature-dependent. Thus, the output of the transducer must be temperature compensated via some type of temperature compensation circuitry. Similarly, if the transducer semiconductor (especially if constructed from silicon) is exposed to light, transient variations can be caused in the pressure readings. Therefore, the semiconductor should be somehow shielded from excessive light exposure.

The accuracy of a semiconductor pressure transducer is also affected by any mechanical stresses that are inadvertently applied to the semiconductor chip. Such stresses can cause transient variations in the pressure reading, thereby decreasing the operational reliability of the transducer apparatus. Thus, the semiconductor pressure transducer must be mounted to the chip carrier such that thermal expansion and contraction of the transducer chip, or other external mechanical stresses, are isolated from the transducer diaphragm.

Finally, the diaphragm of the semiconductor transducer is specifically designed to be of a thickness that is responsive and accurate under a predetermined pressure range, which will be dependent upon the environment in which the transducer will be used. For example, under low pressure situations such as blood pressure monitoring, the diaphragm must be thin enough so as to deflect in response to low pressure pulses transmitted through a fluid catheter line. However, the same blood pressure transducer may be inadvertently subjected to a high transient pressure. Such might be the case where the patient is simultaneously undergoing certain medical procedures—such as an angiogram—which cause a high transient pressure to be present at the pressure transducer due to high injection rates and pressure. Under such circumstances, the blood pressure monitor must be isolated or the diaphragm can be ruptured and the transducer rendered inoperative. Thus, the semiconductor transducer that is designed for a specific pressure range is susceptible to being damaged if it is inadvertently subjected to transient pressures that exceed a critical maximum pressure.

In the past, pressure measurement apparatuses utilizing semiconductor pressure transducers have not addressed each of these characteristics without also diminishing the advantages that are originally sought when using a semiconductor transducer—ease of manufacturing, miniaturization, reliability, and low cost. This can best be appreciated by referring to FIG. 1, which shows a standard implementation of a pressure sensing apparatus using a semiconductor pressure transducer. In prior art devices the pressure transducer chip 2 is mounted to a chip carrier 4 in a manner so as to be positioned directly over a pressure port 6 that is formed through the chip carrier 4. Solder pads 8 (or similar bonding techniques, such as a gold ball bonds or aluminum wedge bonds) are provided on the chip carrier 4 and bonding wires 10 are used to electrically interconnect the transducer chip 2 and the solder pads 8.

As will be appreciated, this electrical interconnect scheme—bonding wires and solder pads—results in a variety of disadvantages. First, a bonding wire and solder pad assembly requires additional surface area to implement, which results in a pressure sensing apparatus that is less conducive to the high-density packaging implementations that are so desirable in a number of applications. Further, as is well known, solder runs like water when overheated, and is brittle and unreliable when applied with an incorrect heat. Consequently, solder pads and bonding wires must be applied via a complex and precise manufacturing process, which adds to the overall cost of the pressure sensing apparatus and increases the chances for manufacturing defects. Solder pads are also less reliable, and may fail over time—especially in extreme environments. Similarly, the bonding wires are difficult to assemble in an automated manufacturing process because they must be placed on the chip one at a time. Further, bonding wires are extremely fragile and are thus subject to breakage during the manufacturing process. Also, the bonding wires are susceptible to breakage once the chip is assembled if the chip is dropped or otherwise subjected to similar forces. Consequently, when connected to the top surface of the transducer chip, the bonding wires must be protected, which is typically accomplished by covering the wires and the top surface with a silicone gel, or similar cap assembly. Again, this is an additional manufacturing step which adds overall cost to the pressure sensor. Finally, the bonding wires themselves can transmit mechanical stresses from the chip carrier to the transducer chip diaphragm and thereby further decrease the overall accuracy of the transducer chip.

As discussed above, a semiconductor pressure transducer must be mounted to the chip carrier such that thermal expansion and contraction of the transducer will not subject the pressure transducer to mechanical stresses which might cause incorrect transient pressure readings. Previously, this was accomplished by mounting the transducer chip on a pedestal (shown as item 12 in FIG. 1) constructed from a material having similar thermal characteristics as the transducer chip, such as pyrex. In this manner, the pedestal 12 will contract and expand with variations in temperature in substantially the same manner as the chip and thereby minimize any mechanical stress which may be caused by the thermal expansion and contraction. However, this adds an additional manufacturing step and increases the cost of the pressure sensing device. Further, the pedestal 12 does not completely solve the problem of isolating the transducer chip from external mechanical forces that may occur from a flexing or bending of the chip carrier. Because the chip is not oriented so as to be coplanar with the substrate, the chip is more susceptible to external forces that may cause inaccurate transient pressure readings.

Figure 1:
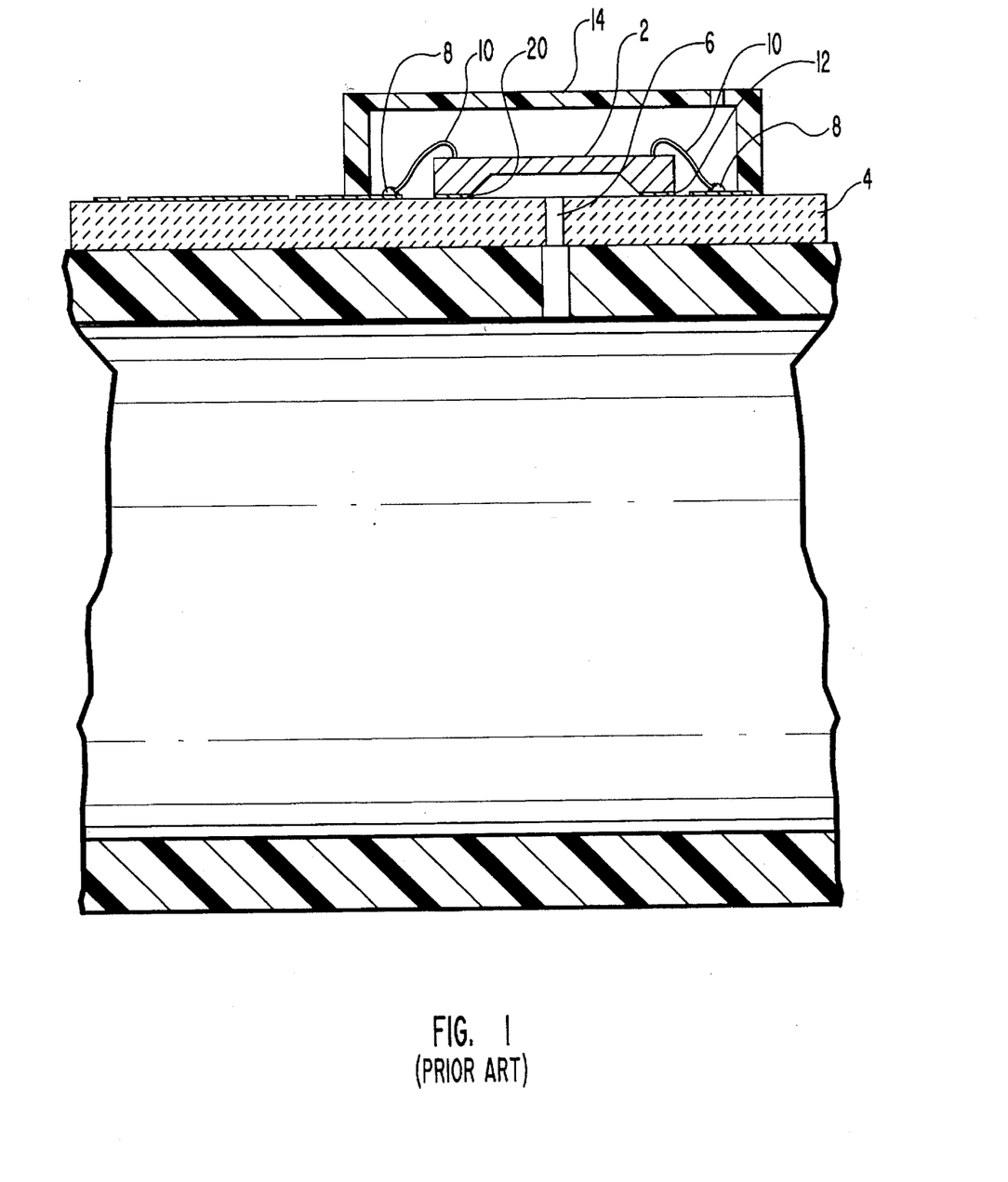
FIG. 1 is a cross-sectional side view of a prior art implementation of a semiconductor pressure transducer assembly illustrating the orientation of the transducer to the fluid pressure source.

As is further illustrated in FIG. 1, in prior art pressure transducers the fluid pressure is transmitted to the transducer diaphragm through a pressure port 6 formed through the chip carrier 4. This physical orientation results in several disadvantages. First, the pressure forces are applied against the transducer 2 so as to urge it away from the chip carrier 4. Thus, if the pressure sensing apparatus is used in a high pressure environment, the transducer chip 2 can potentially be separated from the chip carrier 4 if the adhesive used to hold the chip 2 to the carrier 4 fails. In addition, if the transducer diaphragm is subjected to a high transient pressure, there is the potential for the thin diaphragm to rupture, or otherwise fail because there is nothing to prevent the diaphragm from being displaced past a critical point. As discussed above, in the medical environment, the transducer in a blood pressure monitor may inadvertently be subjected to such a pressure, thereby causing the thin diaphragm to be ruptured or otherwise damaged. Obviously, this renders the transducer inoperable, and medical personnel are at least temporarily deprived of critical blood pressure information. Because semiconductor transducers are physically oriented in the manner shown in FIG. 1, pressure measurement devices in the prior art are subject to these types of failures and are thus less reliable than is desired for medical, as well as many other, applications.

Finally, because prior art semiconductor transducers are mounted on the top side of the chip carrier in the manner shown in FIG. 1, they require additional structure to shield the semiconductor transducer from exposure to light. Typically, this has been accomplished by enclosing the transducer within an opaque housing (14 in FIG. 1) that is attached to the chip carrier 4. Again, this adds additional complexity to the manufacturing process and also results in a device having a larger overall size.

OBJECTS OF THE INVENTION

In light of the foregoing, it is a primary object of the present invention to provide a pressure measurement apparatus that is accurate, reliable, economical, small in size and that is resistant to damage when inadvertently subjected to high transient pressures.

It is therefore an object of the present invention to provide a pressure measurement apparatus that utilizes a semiconductor pressure transducer that is reverse mounted to a chip carrier.

It is a related object of the present invention to provide a pressure measurement apparatus that utilizes a semiconductor pressure transducer that has overpressure protection so that the transducer diaphragm will not be ruptured or otherwise damaged if it is inadvertently subjected to a high transient pressure.

Another object of the present invention is to provide a pressure measurement apparatus that will not be separated from the chip carrier if the apparatus is inadvertently subjected to a high pressure.

Yet another object of the present invention is to provide a pressure measurement apparatus wherein the semiconductor pressure transducer is mounted to a chip carrier in a manner so as to reduce the effect of mechanical stresses on the transducer resulting either from thermal effects or physical movements of the measurement apparatus, thereby insuring the accuracy of the transducer.

Another object of the present invention is to provide a pressure measurement apparatus wherein the semiconductor pressure transducer is mounted to a chip carrier in a manner such that no electrical wires are needed to electrically interconnect the chip carrier to the transducer.

Another object of the present invention is to provide a pressure measurement apparatus that is constructed from a minimum number of component parts and that requires a minimum number of manufacturing steps to assemble, so that the apparatus is easy and low in cost to manufacture.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

BRIEF SUMMARY OF THE INVENTION

To achieve the foregoing objects, and in accordance with the invention as embodied and broadly described herein, a pressure measurement apparatus is provided for measuring a fluid pressure that is generated within a fluid passageway. The apparatus comprises a two-sided dielectric substrate sheet to which is mounted a semiconductor pressure transducer having a circuit side and a cavity side, and a pressure diaphragm formed on the center of the two sides. The circuit side of the pressure diaphragm has a piezoresistive network formed thereon. The circuit side of the pressure transducer is then mounted directly to one side of the dielectric substrate such that the semiconductor transducer is reverse mounted to the substrate, and is thus physically oriented between the fluid passageway and the substrate sheet.

The transducer is encased within a gel cap which contains a substantially incompressible silicone gel. An open end of the gel cap is then positioned so as to be in fluid communication with the fluid passageway, thereby allowing fluid pressures generated within the fluid passageway to be transmitted through the silicone gel to the cavity side of the pressure transducer. Advantageously, the fluid pressure tends to compress the semiconductor transducer against the substrate sheet such that the transducer will not be separated from the substrate under high pressure.

The circuit side of the semiconductor pressure transducer is mounted directly to the surface of the dielectric substrate sheet by way of a series of conductive epoxy bonds. Each epoxy bond is positioned so as to connect a electrical bond pad disposed on the circuit side of the transducer to a corresponding electrical contact on the substrate sheet. In this way, the pressure transducer is both mechanically bonded and electrically connected to the substrate sheet. Significantly, this manner of mounting the transducer to the substrate eliminates any need for electrical bonding wires and thereby saves space, reduces the number of components and greatly facilitates manufacture and assembly of the apparatus. Further, by eliminating the need for electrical bonding wires, the apparatus is not subject to the types of defects and reliability problems often associated with such wiring techniques.

The pressure transducer is bonded to the side of the substrate sheet so that there is a gap between the circuit side and the surface of the substrate, thereby allowing the diaphragm to be displaced when subjected to pressure. However, the diaphragm will only deflect up to a predetermined amount before it will be restricted by the surface of the substrate, or optionally, by an overpressure guard formed on the surface of the substrate sheet opposite to the diaphragm. Significantly, this protects the diaphragm from being ruptured if the transducer is inadvertently subjected to a high transient pressure. Also, the transducer chip is mounted so as to be substantially coplanar with the substrate sheet. Thus, the transducer is free to thermally expand and contract in a substantially uniform manner and is thus not subjected to the uneven mechanical stresses that can distort the transducer's accuracy.

Finally, by reverse mounting the semiconductor transducer chip to the substrate sheet, the light sensitive circuit side of the transducer chip is shielded from direct exposure to excessive amounts of light. Thus, the transducer is further protected from the transient pressure readings that could be caused by exposure to light.

BRIEF DESCRIPTION OF THE DRAWINGS

In order that the manner in which the above-recited and other advantages and objects of the invention are obtained, a more particular description of the invention briefly described above will be rendered by reference to specific embodiments of the invention, which are illustrated in the appended drawings. Understanding that these drawings depict only typical embodiments of the invention and are therefore not to be considered limiting of its scope, the invention will be described with additional specificity and detail through the use of the accompanying drawings in which.

DETAILED DESCRIPTION OF THE PREFERRED EMBODIMENT

It will be readily appreciated that the components of the present invention, as generally described and illustrated in the figures herein, could be arranged and designed in a wide variety of different configurations. Thus, the following more detailed description of the embodiment of the apparatus of the present invention, as represented in FIGS. 2 through 5, is not intended to limit the scope of the invention, as claimed, but it is merely representative of one presently preferred embodiment of the invention.

Figure 2:
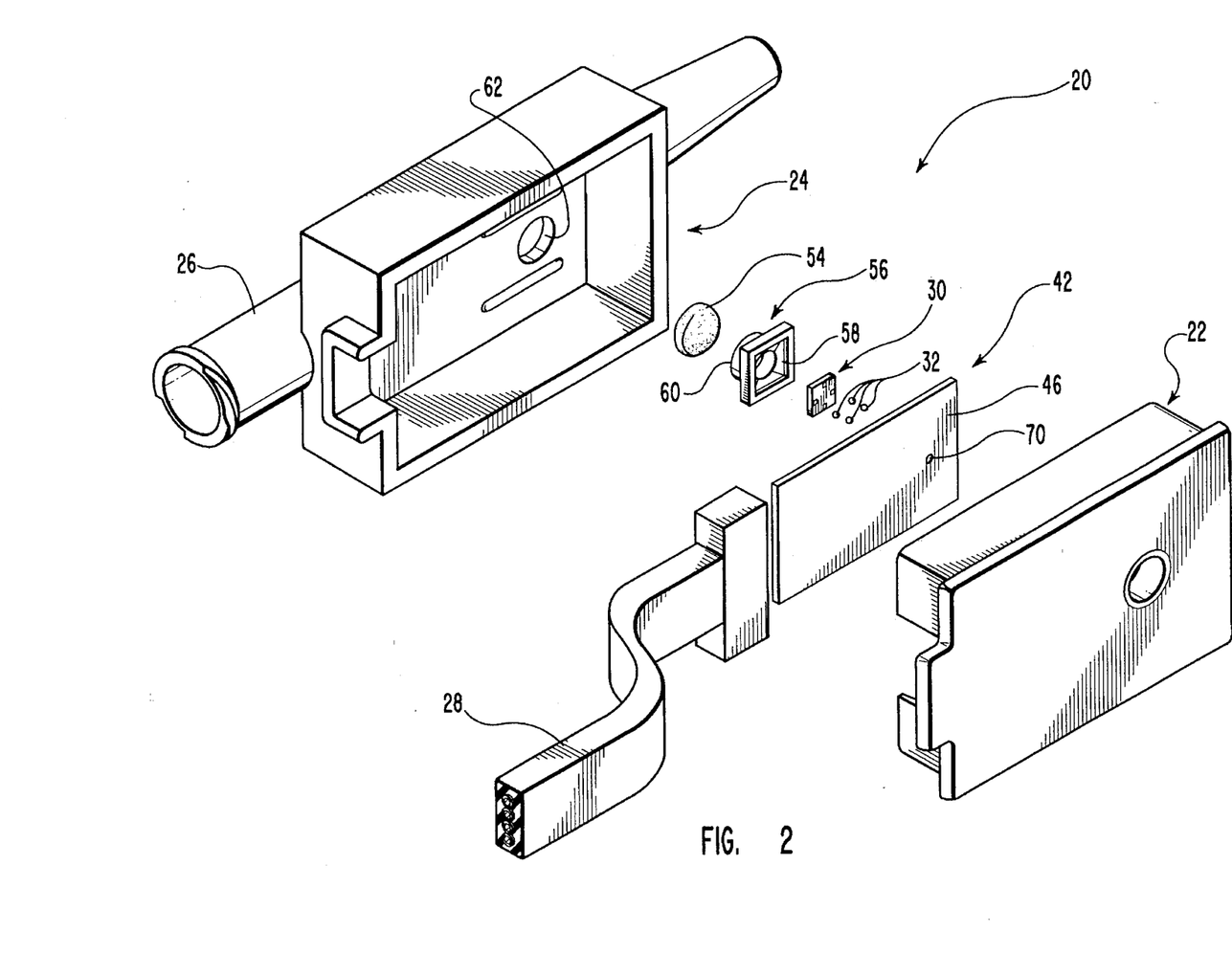
FIG. 2 is a partially exploded perspective view illustrating one presently preferred embodiment of the pressure measurement apparatus of the present invention and a fluid passageway in which the present invention may be used to measure a fluid pressure.

Referring first to FIG. 2, the various pressure sensing components of the pressure sensing apparatus of the present invention, generally designated as 20, are shown. As illustrated, in this embodiment, the components are contained within a housing 22. The housing 22 is attached to a second housing 24 mounted to a fluid passageway, such as a fluid coupling tube 26. By way of example, the fluid coupling tube 26 may be connected to a fluid-filled catheter (not shown) in which case the pressure sensing apparatus 20 can be used to measure, for instance, a patient's blood pressure transmitted through the fluid-filled catheter. In addition, a cable 28 extends from the housing 22 and serves to carry electrical signals which represent the pressure measurements made by pressure apparatus 20 to a monitoring device, such as an electronic display (not shown).

In use, any pressures that are generated within the fluid passageway, such as the fluid coupling tube 26, are detected and measured by the pressure detection components (described in more detail below) contained within the housings 22, 24. The pressure detection components then generate an electrical signal that is representative of the magnitude of the sensed pressures. This electrical signal is then transmitted along the cable 28 to a monitoring device (not shown) such that the pressure data may be appropriately displayed, recorded, or otherwise responded to. It will be appreciated that the pressure measurement apparatus 20 can be used to measure fluid pressures generated within a wide variety of fluid passageways. In addition to blood pressure and other medical applications, the present invention will be suitable for use in other areas as well.

Figure 2A:
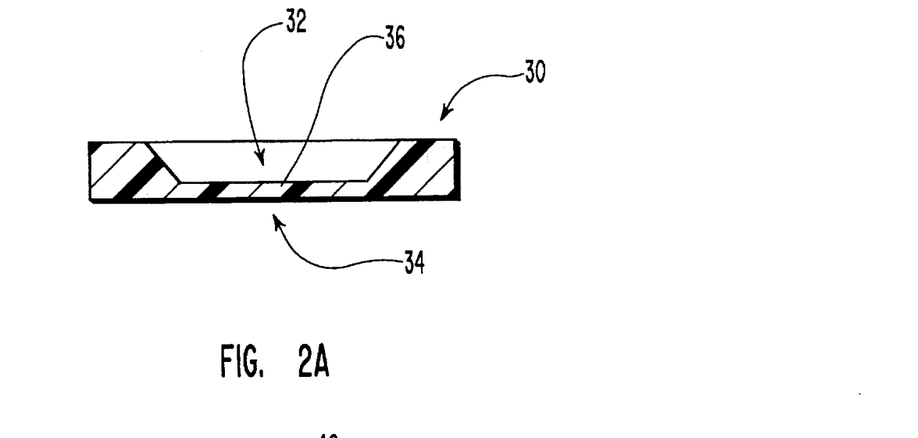
FIG. 2A is an exploded cross-sectional view of the semiconductor pressure transducer of FIG. 2.

With continued reference to FIG. 2, the pressure measurement apparatus 20 is comprised of a pressure sensing means, as for example a semiconductor pressure transducer 30, for sensing the fluid pressure generated within the fluid passageway, and for outputting an electrical pressure signal proportional to the sensed pressure. As can be seen in FIG. 2A, pressure transducer 30 has a cavity side 32 and a circuit side 34, and is fabricated with a diaphragm 36 that is disposed on the center of the cavity 32 and circuit 34 sides. The diaphragm 36 is formed by etching away the central portion of the pressure transducer 30 using standard techniques (such as, for example, by wet or dry etching techniques). In the preferred embodiment, formed on the circuit side 34 of the diaphragm 36 are four piezoresistive elements 37 (shown in FIG. 2B) arranged so as to form a conventional Wheatstone Bridge circuit. The resistive elements 37 are preferably formed by using conventional ion implantation techniques, but could also be formed by other conventional techniques, such as standard diffusion techniques.

The circuit side 34 further has a plurality of electrical bond pads 39 (shown in FIG. 2B) formed thereon, which are each electrically connected to one of the nodes of the Wheatstone Bridge circuit formed on the diaphragm 36. In operation, application of a fluid pressure to the cavity side 32 of the diaphragm 36 will cause it to deflect, and the resulting strain will change the relative resistances of the resistive elements 37. Thus, if a voltage is applied to two of the electrical bond pads 39 which correspond to nodes at diagonally opposite corners of the bridge, the change in resistive values can be detected by measuring the potential difference at the remaining two nodes (connected to the remaining two electrical bond pads 39). Pressure transducer 30 thus provides an output voltage (otherwise referred to as a "electrical signal") between two of the electrical bond pads 39 that is proportional to the applied fluid pressure.

It will be appreciated that the pressure sensing means can be comprised of various forms of pressure transducers and still be within the scope of the invention. For instance, rather than comprising a full Wheatstone Bridge, the diaphragm may have formed thereon a half-bridge circuit configuration, or other similar circuit arrangement. Also, additional circuitry could also be disposed on the semiconductor pressure transducer 30, such as compensation circuitry, thereby adding additional function to the pressure measurement apparatus 20 without requiring additional space.

With continued reference to FIG. 2, it is shown how the pressure measurement apparatus 20 is further comprised of a carrier means for providing a substrate layer, as for example a dielectric substrate sheet 42. Substrate 42 may be formed of any of a number of suitable dielectric materials, such as, for example, a ceramic material. Substrate 42 is formed as a substantially planar layer having a first surface 44 (shown in FIG. 2B) and an opposite second surface 46 (shown in FIG. 2).

Figure 2B:
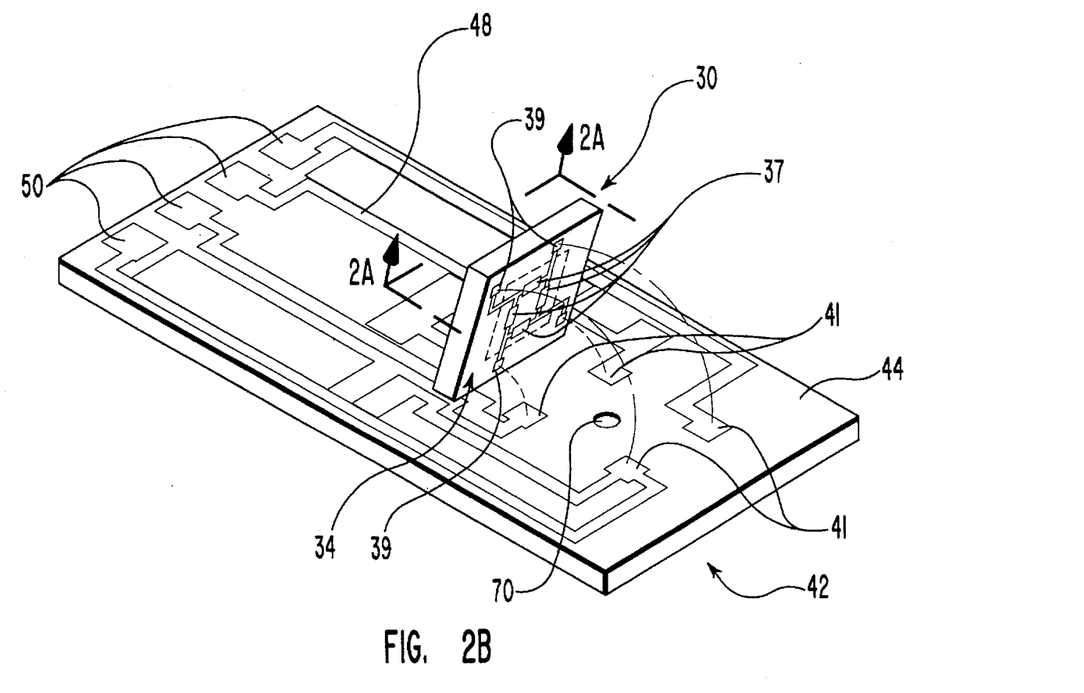
FIG. 2B is a perspective view illustrating the physical orientation of the semiconductor transducer to the substrate sheet.

As is schematically shown in FIG. 2B, substrate 42 is provided with a circuit means, as for example a conventional temperature compensation and zero-offset circuit 48, for adjusting the electrical signal generated by the transducer means. It will be appreciated however that circuit means may also be comprised of a variety of circuit configurations for processing the electrical pressure signal, as for example, amplification circuitry, analog-to-digital conversion circuitry, and digital processing circuitry. Circuit 48 is preferably formed on the first surface 44 of substrate 42. Circuit 48 may also be partially, or completely formed on the second surface 46 of substrate 42 and electrically connected to the first surface 44 via plated through-holes, as is well known in the art. In this manner, multiple circuit components may be disposed on the substrate 42 without requiring additional substrate surface area, thereby allowing for further miniaturization of the pressure measurement apparatus 20. Circuit 48 may be formed in any suitable manner, and preferably is provided using standard silk-screening techniques. Advantageously, by using standard silk-screening techniques, the substrate 42 and the circuit 48 can be manufactured in large quantities, thereby reducing the overall cost of each pressure measurement apparatus 20.

In the preferred embodiment, substrate layer 42 has formed thereon a connector means, such as a series of edge connectors 50, for electrically connecting the substrate 42 to a cable 28. In this way, the pressure apparatus 20 can be connected to an external monitoring device, such as an electronic display (not shown). It will be appreciated that cable 28 can be connected to the edge connectors 50 in a variety of ways. For instance, the cable 28 can be soldered directly to the edge connectors 50, or it can be connected by way of a standard edge connector type device, as is well known in the art.

As can be seen in FIG. 2, the pressure transducer 30 is positioned directly between the substrate 42 and the fluid passageway, such as the fluid coupling tube 26. As is better shown in FIG. 2B and FIG. 3, the circuit side 34 of pressure transducer 30 is connected directly to the first surface 44 of substrate 42 in a substantially coplanar manner. This connection is accomplished with a conductive bonding means, as for example a plurality of electrically conductive bond connections 52 shown in FIG. 5, for electrically connecting and bonding the circuit side 34 to the first surface 44 of substrate 42. Each electrically conductive bond 52 is positioned so as to electrically connect each electrical bond pad 39 disposed on the circuit side 34 of the pressure transducer 30 to a corresponding bond pad 41 disposed on the substrate 42 (as is shown FIG. 2B). In this manner, the plurality of electrically conductive bond connections 52 act not only to physically bond the pressure transducer 30 to the substrate 42, but to electrically connect the transducer 30 to the substrate 42, and the circuitry located thereon, as well.

In the preferred embodiment, the electrically conductive bonds 52 are formed using a "flip chip" bonding method, and are comprised of an electrically conductive polymer produced by Epoxy Technology Inc.® and which are known in the art by the tradename EPO-TEK®. The preferred method for establishing this electrical connection between the pressure transducer 30 and the substrate 42 is set forth in U.S. Pat. No. 5,074,947 and 5,196,371.

This manner of electrically bonding pressure transducer 30 to substrate 42 is advantageous for several reasons. By establishing an electrical connection directly, it eliminates any need for bonding wires and solder pads, which are difficult and expensive to install, are very fragile and thus subject to failure, and which take up additional space. Further, the flip chip bonding process is very conducive to an automated, high volume, low cost fabrication process, thereby resulting in a pressure measurement apparatus 20 that has a lower unit price.

Figure 4:
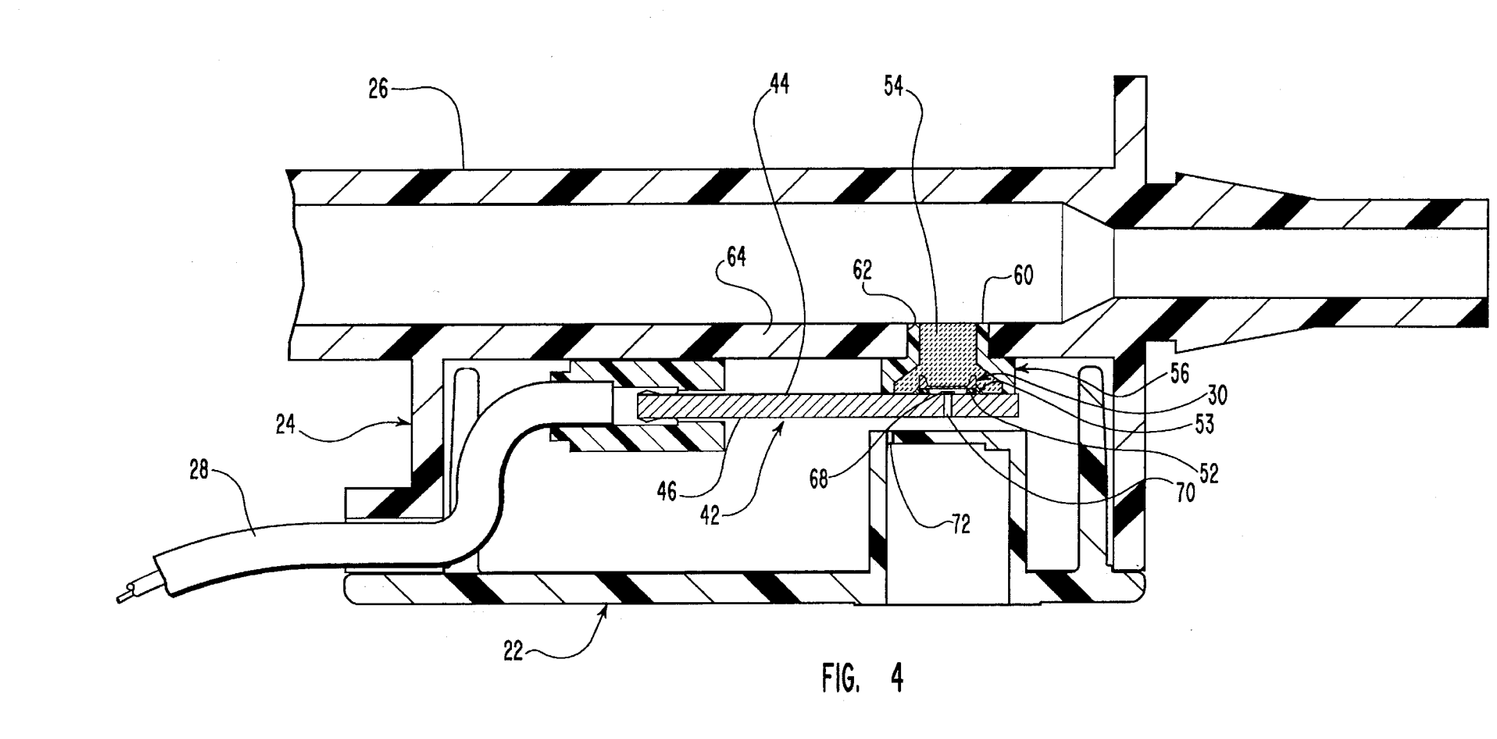
FIG. 4 is a cross-sectional view of the pressure measurement apparatus when mounted to the fluid passageway of FIG. 2.
Figure 5:
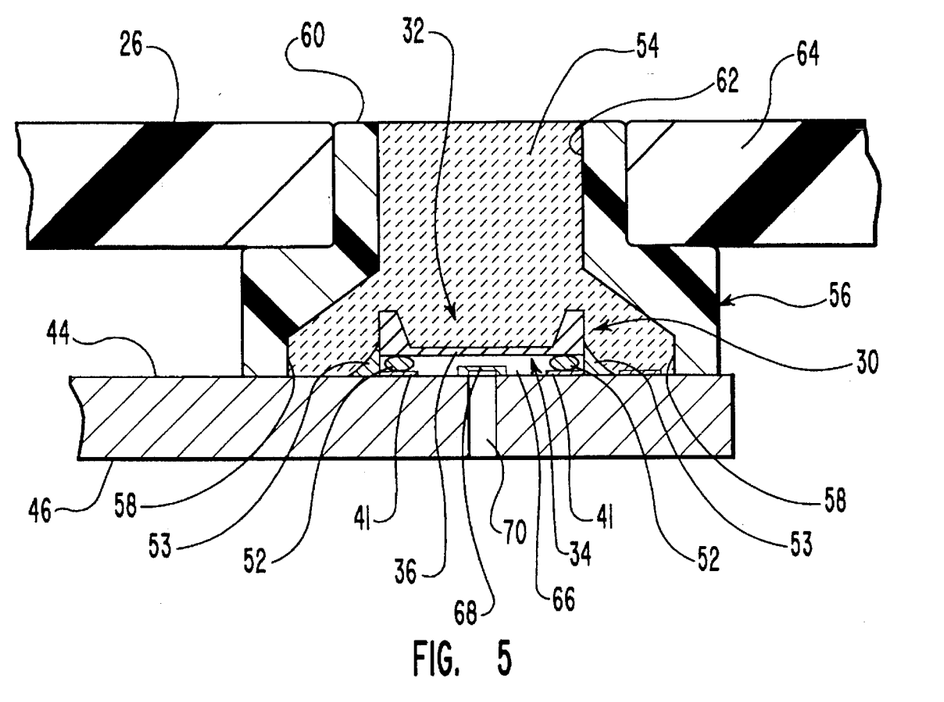
FIG. 5 is an enlarged version of the cross-sectional view shown in FIG. 4.

As is further depicted in FIGS. 4 and 5, once the transducer 30 is electrically bonded to the substrate 42, the apparatus 20 further comprises a sealing means for securing the circuit side 34 of the transducer 30 to the first surface 44 of the substrate 42 in a manner such that a fluid-tight gap 66 is formed between the circuit side 34 and the first surface 44. The sealing means comprises, for example, a layer of soft, pliable epoxy 53 that is placed around the bottom periphery of the pressure transducer 30 and the first surface 44 of the substrate 42. In this way, fluids (such as may be present in the fluid passageway or transmitting means discussed below) are prevented from entering the gap 66 between the circuit side 34 and the first surface 44. The sealing means also acts to further bond the transducer 30 to the substrate 42.

Once mounted to the substrate 42, the cavity side 32 of the pressure transducer 30 is placed in fluid communication with a fluid passageway, such as the fluid coupling tube 26 shown in FIGS. 2, 3, 4 and 5. As used herein, the term "fluid communication" is intended to mean the pneumatic or hydraulic transmission (direct or indirect) of fluid pressures exerted within a fluid passageway so that such fluid pressures can be sensed by the pressure transducer 30. Direct transmission of such fluid pressures would occur, for example, when the diaphragm 36 of the pressure transducer 30 is placed into contact (either pneumatically or hydraulically, or a combination of both) with a fluid contained in a fluid passageway. Indirect transmission could be said to occur, for example, where the transducer diaphragm is coupled to another diaphragm or similar medium that in turn contacts the fluid contained in the fluid passageway.

In the embodiment of FIGS. 2–5, the cavity side 32 is placed in an indirect fluid communication with the fluid contained in the fluid passageway, or coupling tube 26, by way of a transmission means, as for example a substantially incompressible gel medium 54. In this way, the fluid within the fluid passageway is not allowed to directly contact the pressure transducer 30. Further, the gel medium 54 may be electrically nonconductive so as to electrically isolate the transducer from the fluid contained within the fluid passageway, which may be important in certain applications.

The substantially incompressible gel medium 54 serves to couple the fluid pressures generated within the fluid passageway to the cavity side 32 of transducer 30, so as to cause a corresponding deflection of the diaphragm 36. In the preferred embodiment the incompressible gel medium 54 is comprised of a silicone gel. It will be appreciated however that, depending on the environment, the transmitting means could also be comprised of other substances that will permit transmission of pressure fluid pressures within the fluid passageway to the diaphragm 36. For instance, in some applications, the transmitting means could be comprised of air.

Figure 3:
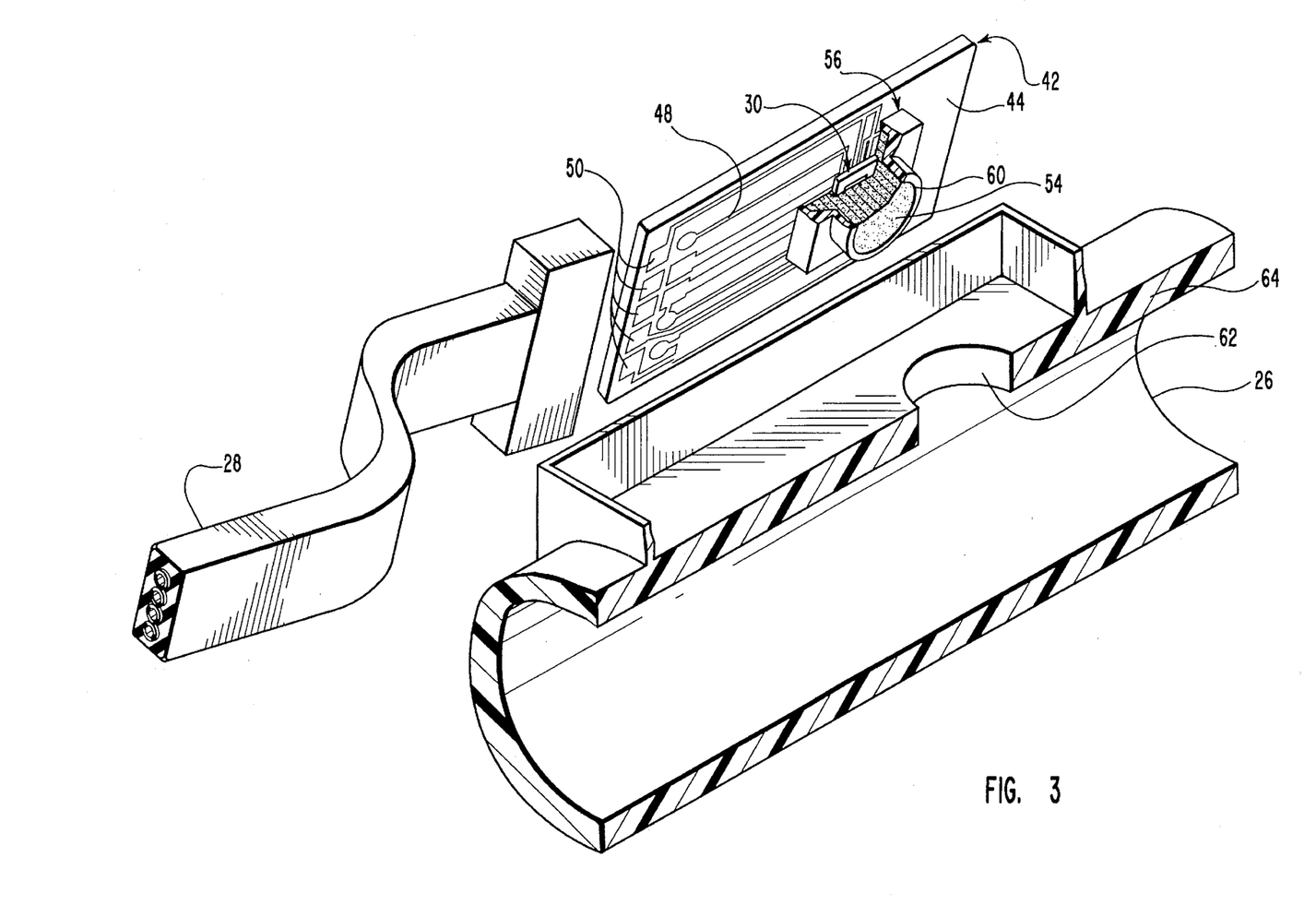
FIG. 3 is a perspective view illustrating the physical orientation of the pressure measurement apparatus to the fluid passageway illustrated in FIG. 2.

As is depicted in FIGS. 3 through 5, the incompressible gel medium 54 is preferably disposed within a gel cap 56. The gel cap 56 has a generally square shaped first open end 58 (best seen in FIG. 2) that is mounted to the first surface 44 of the substrate 42 in a manner so as to completely enclose the pressure transducer 30 (illustrated in FIG. 3). The first open end 58 is mounted to the substrate 42 using any suitable adhesive (not shown). Gel cap 56 further has a generally cylindrically shaped second open end 60 (best seen in FIG. 3). The second open end 60 is preferably shaped so as to be received in a tight fitting manner within a pressure port 62 formed within a wall 64 of the fluid passageway, such as the fluid coupling tube 26, as is best seen in FIG. 4. Second open end 60 is preferably held within the pressure port 62 by way of a suitable adhesive. In this manner, the substrate 42 and pressure transducer 30 assembly are structurally supported, and held in fluid communication relative to the fluid coupling tube 26, solely by the gel cap 56. Advantageously, this eliminates the need for any additional structural supports and further reduces the space and materials required for the pressure measurement apparatus 20.

As is further depicted in FIGS. 4 and 5, pressure transducer 30 is reverse mounted to substrate 42 such that the circuit side 34 and the first surface 44 are substantially coplanar, except for a substantially uniform gap 66 disposed therebetween. In this way, the diaphragm 36 is capable of being deflected when fluid pressure is exerted on it via the incompressible gel medium 54. Advantageously, gap 66 is of sufficient width so that the diaphragm 36 is free to deflect and thereby detect a wide range of fluid pressures. At the same time, diaphragm 36 will not deflect greater than the distance defined by gap 66, regardless of the fluid pressure applied, because it will abut against the first surface 44. In this way, the relatively thin diaphragm 36 will not rupture, or be otherwise damaged, if it is inadvertently subjected to an overly high transient fluid pressure—as is commonly the case in many applications. Thus, there is an inherent overpressure protection that results from the physical orientation of pressure transducer 30 and substrate 42.

In the event that gap 66 does not provide sufficient overpressure protection (i.e., it permits the diaphragm 36 to deflect to the point of rupturing), then the pressure measurement apparatus 20 may optionally be supplied with an overprotection means, as for example an overprotection guard 68, best illustrated in FIG. 5. The overprotection means is also for preventing the pressure transducer from being damaged when it is subjected to a pressure that is greater than a predetermined maximum pressure. As is shown, the overprotection guard 68 is a substantially planar portion that is formed on the first surface 44 of the substrate 42 so as to be adjacent to, and spaced apart from the midpoint of the diaphragm 36. The overprotection guard 68 is a height adjustment mechanism that prevents the diaphragm 36 from being deflected past a critical point, as defined by the height of the overprotection guard, because it will abut against the guard 68 once it deflects to that position. Again, this protects the pressure transducer 30 from being damaged if it is inadvertently or otherwise subjected to excessively high transient pressures.

In addition to overpressure protection, the physical orientation of the transducer 30 to the substrate 42 is advantageous for other reasons. Because the transducer 30 is oriented between the fluid passageway and the substrate 42, the fluid pressures will act so as to compress the transducer 30 against the substrate 42. Thus, regardless of the magnitude of the fluid pressure, the transducer 30 will not be inadvertently separated from the substrate 42. This contrasts with the prior art devices wherein the fluid pressures acted so as to force the transducer away from the substrate (See FIG. 1), thereby resulting in the potential for the transducer to separate from the substrate and thus be rendered inoperable.

Further, because the pressure transducer 30 is reverse mounted to substrate 42 such that the circuit side 34 and the first surface 44 are substantially coplanar, mechanical stresses are more evenly distributed across the transducer 30. Thus, for example, transducer 30 is able to thermally expand and contract without producing an uneven force on the diaphragm 36 and thereby cause an incorrect, transient pressure reading. Similarly, the coplanar orientation helps isolate the diaphragm 36 from uneven mechanical stresses or torques that might otherwise result from the flexing or bending of substrate 42.

The pressure measurement apparatus is further comprised of a venting means for venting the semiconductor pressure transducer 30 to some substantially constant pressure. The venting means may be comprised of, for example, a vent hole 70 (shown in FIG. 2B and FIGS. 4–5) that is formed through the substrate layer 42 (if the substrate layer is also comprised of an overprotection guard, the vent hole 70 may also be formed through the overprotection guard 68, as shown in FIG. 5). The diaphragm 36 on the circuit side 34 of the transducer 30 overlies the vent hole 70 so that the pressure measured by the transducer 30 is referenced to any pressure to which the vent hole 70 is exposed. The vent hole 70 can be exposed directly to a constant pressure, for example, by merely forming a second hole 72 (shown in FIG. 4) in the first housing 22 and thereby exposing it to atmospheric pressure, or by providing a reference pressure via the cable 28, or by exposing the vent hole 70 to some other predetermined pressure. Alternatively, the venting means could be comprised of, for example, a hollow tube having one end formed through the substrate layer, and an opposite end exposed to a substantially constant pressure. In this manner, the tube may be used to calibrate the transducer.

From the above discussion, it will be appreciated that the present invention provides a pressure measurement apparatus that is accurate, reliable and low in cost. Since the semiconductor pressure transducer is reverse mounted to the substrate sheet by using a flip-chip bonding technique, fragile bonding wires and solder pad connections are completely eliminated. This eliminates expensive manufacturing steps, reduces the number of component parts required, and increases the reliability of the apparatus. Additionally, by reverse mounting the semiconductor transducer to the substrate sheet, the fragile transducer diaphragm is protected from being ruptured or otherwise damaged when subjected to exceedingly high transient pressures. Also, the transducer will not be separated from the substrate sheet under high pressures. Further, the reliability of the apparatus is increased because the transducer is mounted to the substrate sheet in a substantially coplanar manner, and is thus less susceptible to transient pressure readings otherwise caused by thermal expansion and/or external stresses. Also, the transducer is protected by the substrate sheet from excessive exposure to light, further increasing the accuracy of the pressure measurement apparatus.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. A pressure measurement apparatus for use in the measuring of a fluid pressure generated within a fluid passageway, the pressure measurement apparatus comprising:

carrier means for providing a substrate and having (i) a first surface with a first circuit means for electrically processing an electrical signal proportional to sensed fluid pressures, said first surface also comprising an overpressure guard means for preventing diaphragm flexture beyond a selected limit, and (ii) an opposite second surface, said carrier means being mounted in relation to said fluid passageway such that said first surface with said circuit means is facing toward said fluid passageway;

pressure sensing means for sensing the fluid pressure generated within said fluid passageway and for out putting an electrical signal proportional to the sensed fluid pressure, said pressure sensing means having a non-planar cavity side to which the fluid pressure is applied and a planar circuit side comprising a second circuit means for detecting the applied fluid pressure and for out putting said proportional electrical signal, and wherein said pressure sensing means is mounted such that said planar circuit side is facing away from said fluid passageway and toward said first surface with said first circuit means, but said non-planar cavity side is facing toward said fluid passageway, and wherein said pressure sensing means is centrally positioned over said overpressure guard means such that said guard means is positioned essentially at the center of said planar circuit side;

overpressure protection means for preventing the pressure sensing mean from being damaged when subjected to a fluid pressure that is higher than a predetermined maximum pressure; and conductive bonding means for bonding the pressure sensing means to the carrier means and for electrically connecting the second circuit means disposed on said circuit side of the pressure sensing means to the first circuit means disposed on said first surface of the carrier means.

2. An apparatus as defined in claim 1 wherein the pressure sensing means comprises a semiconductor pressure transducer comprising:

a piezoresistive pressure sensitive diaphragm disposed on the center of the cavity and circuit sides; and a plurality of electrical bond pads disposed on the circuit side and electrically connected to said piezoresistive diaphragm.

3. An apparatus as defined in claim 2 wherein the conductive bonding means comprises a plurality of electrically conductive bonds, each of said electrically conductive bonds formed from a conductive material and oriented so as to be aligned with a corresponding electrical bond pad disposed on said circuit side so as to form an electrical connection between each of said bond pads and the substrate.

4. An apparatus as defined in claim 3 further comprising a substantially incompressible gel medium disposed between the cavity side of said semiconductor pressure transducer and the fluid passageway, whereby the cavity side is in fluid communication with the fluid passageway.

5. An apparatus as defined in claim 4 wherein the gel medium is contained within a gel cap, the gel cap comprising:

a first open end mounted to the first surface of the sheet of dielectric substrate in a manner so as to have the semiconductor pressure transducer disposed therein; and a second open end positioned so as to be in fluid communication with the fluid passageway.

6. An apparatus as defined in claim 5 further comprising means for venting the semiconductor pressure transducer to some substantially constant pressure.

7. An apparatus as defined in claim 6 wherein the venting means comprises a vent hole, the vent hole being formed through the substrate so as to extend from the second surface to the first surface and exiting the first surface at a point that is overlaid by the circuit side of the pressure sensing means, the vent hole being exposed to a substantially constant pressure such that the semiconductor pressure transducer is continuously vented to said substantially constant pressure.

8. An apparatus as defined in claim 1 wherein the substrate further comprises connector means for electrically connecting the sheet of dielectric substrate to a cable, whereby said electrical signal can be transmitted to a monitoring device.

9. A pressure measurement apparatus that is useable in a body fluid pressure measurement system having an indwelling, fluid-filled catheter inserted into a patient, the fluid-filled catheter being in fluid communication with a fluid passageway, a wall of the fluid passageway having a pressure port formed therein so as to provide a fluid communication with the interior of the fluid passageway, the pressure measurement apparatus comprising:

(a) a substantially planar sheet of dielectric substrate comprising:
  (i) a first planar surface oriented to face toward said fluid passageway;
  (ii) a second planar surface opposite to the first surface; and
  (iii) a vent hole formed completely through the sheet of dielectric substrate;

(b) a semiconductor pressure transducer having a cavity side and a circuit side mounted such that said cavity side is facing toward said fluid passageway and said circuit side is facing toward said first planar surface of the substrate, and further including:
  a piezoresistive pressure sensitive diaphragm disposed on the center of the cavity and circuit sides; and
  a plurality of electrical bond pads disposed on the circuit side and electrically connected to said piezoresistive diaphragm;

(c) overpressure protection means for preventing the piezoresistive pressure sensitive diaphragm from being damaged when subjected to a fluid pressure that is higher than a predetermined maximum pressure:

(d) conductive bonding means for electrically connecting each of said electrical bond pads disposed on the circuit side of the semiconductor pressure transducer to the first surface of the sheet of dielectric substrate in a manner such that the semiconductor pressure transducer is positioned between the pressure port and the sheet of dielectric substrate, whereby the semiconductor pressure transducer is reverse mounted to the sheet of dielectric substrate; and (e) means for transmitting the fluid pressure generated within the fluid-filled catheter between the fluid passageway and the cavity side of the semiconductor pressure transducer.

10. An apparatus as defined in claim 9 further comprising means for sealing the circuit side of the semiconductor pressure transducer to the first surface of the sheet of dielectric substrate means in a manner such that there is a fluid-tight gap formed between the circuit side and the first surface.

11. An apparatus as defined in claim 9 wherein the conductive bonding means comprises a plurality of electrically conductive bonds, each of said electrically conductive bonds formed from a conductive material and being oriented so as to be aligned with a corresponding electrical bond pad disposed on said circuit side so as to form an electrical connection between each of said bond pads and the sheet of dielectric substrate.

12. An apparatus as defined in claim 9 wherein the pressure transmitting means comprises a substantially incompressible and nonconductive gel medium disposed between the cavity side of the semiconductor pressure transducer and the fluid passageway, whereby the cavity side is in fluid communication with the fluid passageway.

13. An apparatus as defined in claim 12 wherein the gel medium is contained within a gel cap, the gel cap comprising:

a first open end mounted to the first surface of the sheet of dielectric substrate in a manner so as to have the semiconductor pressure transducer disposed therein; and a second open end secured within said pressure port so as to be in fluid communication with the fluid passageway.

14. An apparatus as defined in claim 9 wherein the sheet of dielectric substrate further comprises circuit means for adjusting the electrical signal generated by the semiconductor pressure transducer.

15. An apparatus as defined in claim 9 wherein the sheet of dielectric substrate further comprises connector means for electrically connecting the sheet of dielectric substrate carrier means to a cable, whereby said electrical signal can be transmitted to a monitoring device.

* * * * *